United States Patent [19]
Kotz et al.

[11] Patent Number: 5,108,453
[45] Date of Patent: Apr. 28, 1992

[54] BONE IMPLANT

[75] Inventors: Rainer Kotz, Wein; Werner Kaltenbrunner, St. Marein, both of Austria

[73] Assignee: Boehler GmbH, Kapfenberg, Austria

[21] Appl. No.: 493,112

[22] Filed: Mar. 15, 1990

[30] Foreign Application Priority Data

Mar. 16, 1989 [AT] Austria .................. A602/89

[51] Int. Cl.⁵ .............................................. A61F 2/36
[52] U.S. Cl. ...................................................... 623/23
[58] Field of Search ................... 623/16, 18, 19, 20, 623/22, 23

[56] References Cited

U.S. PATENT DOCUMENTS 3,067,740 11/1962 Haboush ........................... 623/23
4,784,124 11/1988 Kaltenbrunner ................. 623/23

FOREIGN PATENT DOCUMENTS 3003051 7/1981 Fed. Rep. of Germany .

Primary Examiner—David Isabella
Attorney, Agent, or Firm—Fleit, Jacobson, Cohn, Price, Holman & Stern

[57] ABSTRACT

The invention relates to a bone implant for joint endoprostheses with a collarless, truncated-cone-shaped shaft (3) which can be inserted into a recess (1) of a bone (2) and which supports a joint piece (7), which shaft (3) has a surface area (8) with a plurality of protrusions (9). It is provided by the invention that the protrusions (9) are formed by local teeth rising from the surface area (8), the distal areas of which have at least one cutting or abrading edge or surface (10) for abrading the bone (2) during insertion or for creating a space for the protrusions (9) so that they can be placed into the bone (2).

28 Claims, 3 Drawing Sheets

FIG. 3
FIG. 4
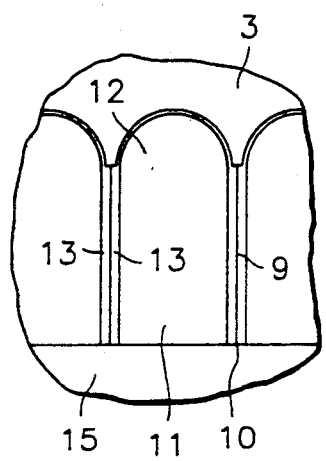
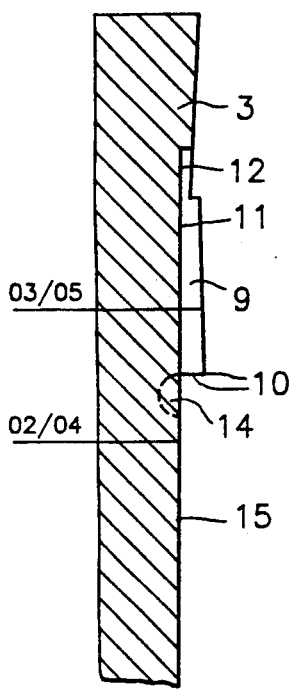
FIG. 5
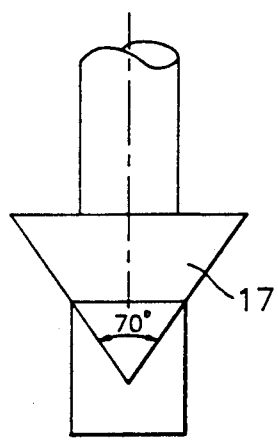
FIG. 6
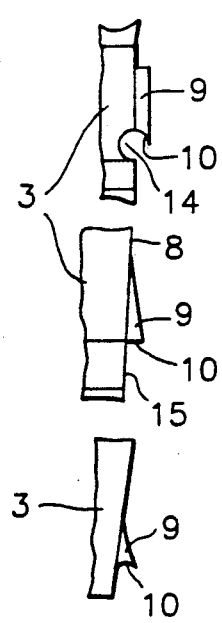
FIG. 7
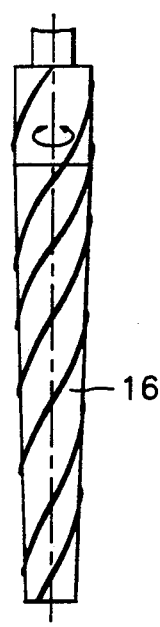

BONE IMPLANT

FIELD OF THE INVENTION

The invention relates to a bone implant for joint endoprostheses for the human locomotor system, in particular locomotor apparatus, with a shaft which can be inserted into a recess of a bone, which has a total cross sectional surface which increases, at least over a part thereof, from the distal to the proximal end, is in particular without a collar, elongated and preferably generally in the form of a truncated cone, which supports in the area of its proximal end a joint or joint piece by means of an intermediate piece, either in one piece or specially formed and which, in particular metallic, shaft can be preferably anchored in the bone primarily stable and has a surface area which can be brought into contact, preferably free of bonding agents, with the bone and which has a plurality of protrusions which are preferably all of the same type and which in general preferably point radially outwardly away from the main shaft axis.

BACKGROUND OF THE INVENTION

Elongated joint implants are known, which can be inserted into tubular bones, in which the cross section decreases from the proximal to the distal end in order to adapt the shaft to the actuality of the bone or to reduce the amount of material to be removed when preparing the recess for receiving the implant.

To anchor the implant in the bone, on the one hand the use of bonding agents, for example on a plastic basis, has become known or, on the other, techniques operating without bonding agents for anchoring which, in case of direct anchoring, prevent problems caused by heat generation and incompatibility of the tissue with the bonding agent. However, the desired goal is to avoid a prolonged waiting period required for the implant to grow in after insertion of the shaft part and to obtain, immediately after the implant has been inserted, a stable connection between shaft and bone.

The recess in the bone for receiving the shaft of the implant is generally formed by driving a rasp, cutter or broaching tool which generally corresponds to the shape of the shaft, into the bone in the direction of the diaphysis. If the various known implant shafts, which mostly have curved shapes, adjoin the walls of the recess only in a few places and over relative short areas, the transfer of the mechanical forces occurs in these areas across zones with comparatively small surfaces and therefore with a high pressure load. However, such pressure spots cause a disruption of the biological balance inside the bone, to which it reacts in that in these areas of increased pressure stress a breakdown of the bone substance takes place and thus a weakening of the cortex and therefore the danger of a loosening of the seat of the shaft.

Placement of longitudinally extending ribs on the surface areas of the shafts does not remove this problem. Although the edges penetrate into the bone tissue, they laterally displace it so that this also causes increased pressure stresses which, because of the linear load on the bone, can burst it. Furthermore, the contact area between the bone and the shaft of the implant is not noticeably increased by this method; in such a case only the longitudinally extending ribs, not the surface area, adjoin the bone or penetrate it.

SUMMARY OF THE INVENTION

It is an object of the present invention to design a bone implant of the type indicated above in such a way that, along with simple insertion into the recess in the bone, as large as possible a contact of the surface area of the shaft on the inside of the recess in the bone is made possible and that additionally the highest degree of protection against axial torsion, along with satisfactory physiological compatibility and a high degree of suitability for extended use are provided.

This object is attained in accordance with the invention in connection with a bone implant of the type previously mentioned in that the protrusions are formed by teeth locally rising from the surface area, the distal areas of which have, for the purpose of cutting or abrading the bone during insertion or for creating a space for the protrusions so that they can be placed into the bone, at least a cutting or abrading edge or surface or which are in the shape of cutting or abrading edges or surfaces.

The implant according to the invention only requires the provision of a rotationally symmetrical recess in the bone, by which already a high degree of coincidence between the shape of the inner wall of the recess and the surface area of the shaft can be attained. When inserting the implant, the teeth or protrusions provided in the surface area remove the bone material in a distal direction and do not laterally displace it. This removal of the bone material during insertion prevents the formation of mechanical stresses in the bone. At the same time the implant is secure against torsion. The relatively short teeth only take off the bone over short stretches, i.e. over areas in general corresponding to the long extension of the teeth, so that unnecessary weakening of the bone is avoided. But the penetration of the teeth into the bone does not prevent the satisfactory close contact of the surface area of the shaft of the inserted implant with the inner wall surface of the recess.

It is preferred for the shaft of the implant to have a cylindrical and a cone-shaped shaft section, the cone-shaped shaft section being longer than the cylindrical shaft section and the protrusions preferably being formed in the cone-shaped shaft section of the implant, if applicable the protrusions being disposed in two peripheral rows, extending in particular parallel to each other. In this connection it is practical to locate the peripheral rows of protrusions approximately in the area of the first and second thirds of the length of the cone shaped shaft. Sufficient support against torsion is provided by means of this disposition of the teeth and the implantation of the shaft of the prosthesis is performed in a manner which is easy on the bone.

It has been shown to be advantageous if the height of the protrusions above the surface area is 0.2 to 1 mm, preferably 0.3 to 0.6 mm. In this connection it is practical if the protrusions, which are disposed at distances from each other over the periphery of the cone-shaped shaft section, are at a distance determined by a central angle of between 10° and 35°, preferably 15° to 30°. This design, combined with a regular placement of the teeth over the periphery of the shaft section, makes possible simple manufacture of the implant, simple insertion into the prepared recess in the bone and provides sufficient support.

To receive the bone material shaved off by the teeth or pushed ahead by them it is advantageous if, preferably following the distal end area of the protrusions in the cone-shaped shaft section, an annular depression or annular groove is formed, or if, following the distal end area of the protrusions or the annular groove, the cone-shaped shaft section is shaded or reduced into a cylindrical peripheral shaft area, the length of which approximately corresponds to the long extension of the protrusions. In this way receptacles or depositories for the bone material are created which simultaneously allow the growth of the bone into the recesses of the prosthesis, by means of which the resistance against pulling the shaft out is increased.

If the areas between the individual protrusions are flat or if these flat areas are extended in their proximal end area by surface areas which are in the shape of segments of a circle, essentially semicircular, and are located on the same radial level, manufacture of the teeth is made possible in a simple way by means of an angular milling cutter which, in this case, need only be moved parallel to the main axis of the shaft for forming the individual teeth.

Further preferred embodiments ensue from the following description, the drawings and the patent claims. The invention will be described below by way of example by means of the drawings.

protrusions 9 facing the distal end of the shaft 3 are in the form of cutting surfaces or cutting edges 10.

FIG. 1a shows an implant in an enlarged scale, the dimensions of the individual areas of the implant as shown in the following table can be seen from this FIG. The dimensions shown are the dimensions of preferred embodiments.

TABLE

| D | d | L | HL | D1 | L1 | L2 | D2 | D3 | L3 | D4 | D5 | at D3 | | | at D5 | | |
|---|---|---|---|---|---|---|---|---|---|---|---|---|---|---|---|---|---|
| | | | | | | | | | | | | Z | α | T | Z | α | T |
| 18 | 5 | 135 | 53 | 9 | 90 | 27 | 11,1 | 12,5 | 58 | 14,2 | 15,6 | 12 | 30,0 | 0,64 | 15 | 24,0 | 0,61 |
| 19 | 6 | 135 | 54 | 10 | 90 | 27 | 12,1 | 13,5 | 58 | 15,2 | 16,6 | 13 | 27,69 | 0,63 | 16 | 22,5 | 0,60 |
| 20 | 6 | 145 | 54 | 10 | 100 | 27 | 12,1 | 13,5 | 68 | 16,2 | 17,6 | 13 | 27,69 | 0,63 | 17 | 21,18 | 0,59 |
| 21 | 6 | 145 | 55 | 11 | 100 | 27 | 13,1 | 14,5 | 68 | 17,2 | 18,6 | 14 | 25,71 | 0,62 | 18 | 20,0 | 0,59 |
| 22 | 7 | 145 | 56 | 12 | 100 | 27 | 14,1 | 15,5 | 68 | 18,2 | 19,6 | 15 | 24,0 | 0,61 | 19 | 18,95 | 0,58 |
| 23 | 8,5 | 150 | 56 | 12,5 | 105 | 33 | 15,2 | 16,6 | 74 | 19,3 | 20,7 | 16 | 22,5 | 0,60 | 20 | 18,0 | 0,58 |
| 24 | 8,5 | 160 | 57 | 12,5 | 115 | 33 | 15,2 | 16,6 | 74 | 19,3 | 20,7 | 16 | 22,5 | 0,60 | 20 | 18,0 | 0,58 |
| 25 | 8,5 | 165 | 58 | 13 | 120 | 38 | 16,2 | 17,6 | 80 | 20,4 | 21,8 | 17 | 21,18 | 0,59 | 21 | 17,14 | 0,58 |
| 26 | 9 | 165 | 59 | 14 | 120 | 38 | 17,2 | 18,6 | 80 | 21,4 | 22,8 | 18 | 20,0 | 0,59 | 22 | 16,36 | 0,57 |
| 27 | 9 | 165 | 60 | 15 | 120 | 38 | 18,2 | 19,6 | 80 | 22,4 | 23,8 | 19 | 18,95 | 0,58 | 23 | 15,65 | 0,57 |

BRIEF DESCRIPTION OF THE DRAWINGS

FIG. 3 is a top view and FIG. 4 a longitudinal view in accordance with detail B in FIG. 1a, FIG. 5 is an angular milling cutter such as can be used for making teeth, for example in accordance with FIG. 2, FIG. 6 are various embodiments of teeth and FIG. 7 is a tool for making a cone-shaped recess in the bone.

DETAILED DESCRIPTION OF THE PREFERRED EMBODIMENTS

Figure 1:
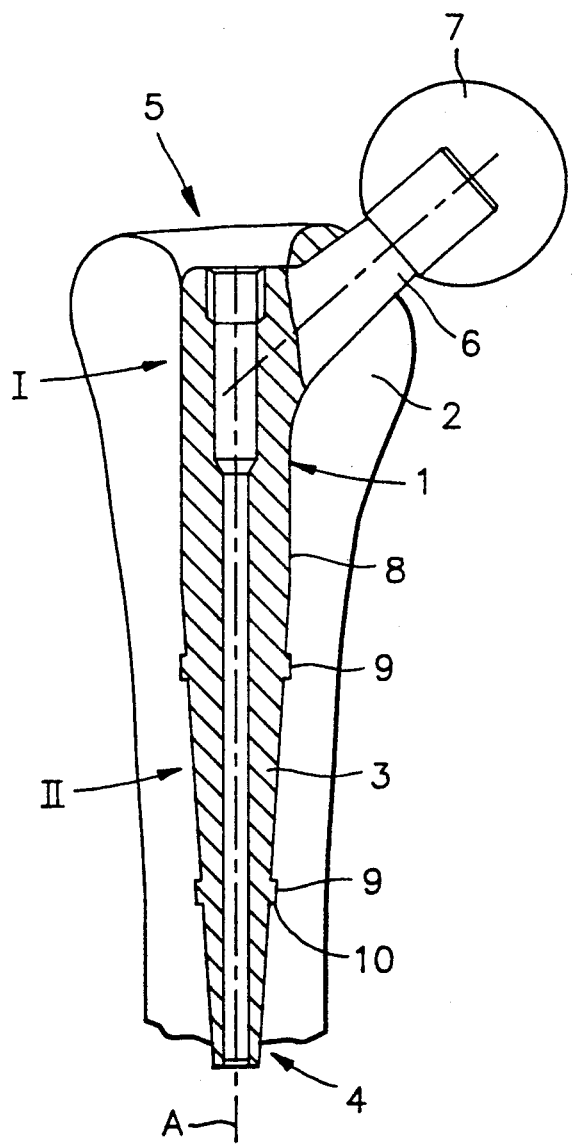
FIG. 1 is a schematic view of an implant inserted into a bone.
Figure 1A:
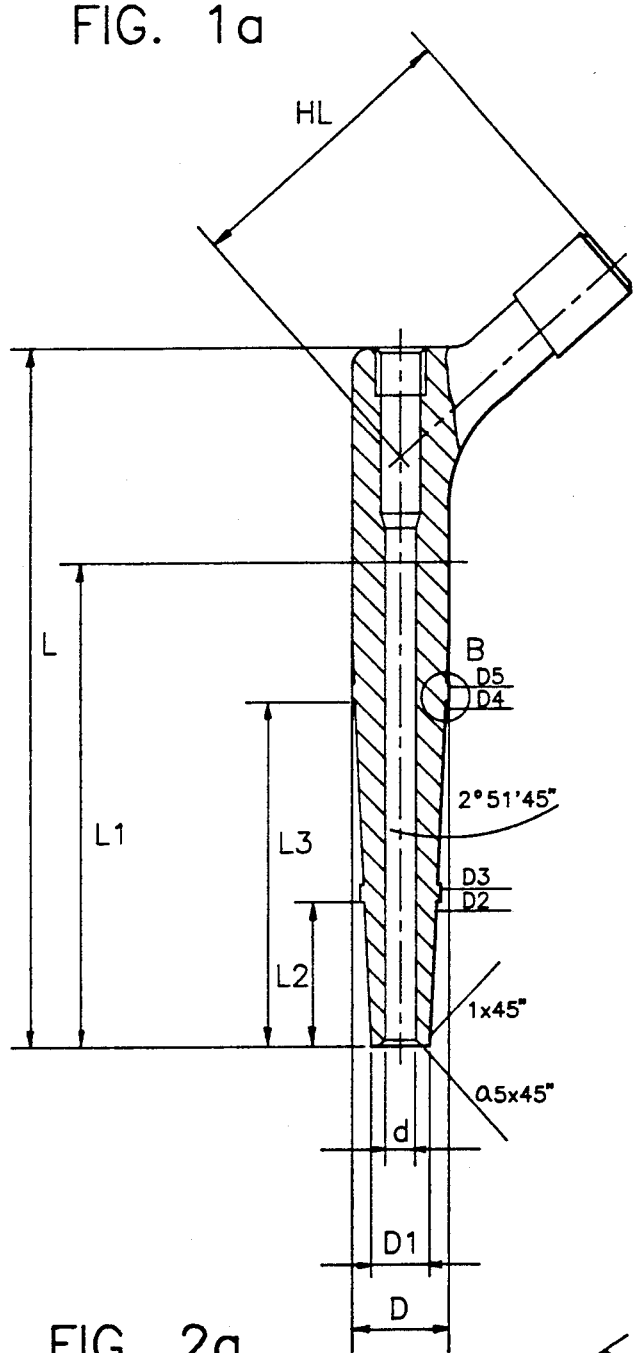
FIG. 1a is an enlarged view of the implant.
Figure 2A:
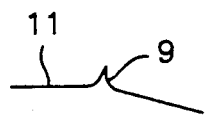
FIGS. 2 and 2a are partial sections through the shaft of an implant at the height of the row of teeth.
Figure 2:
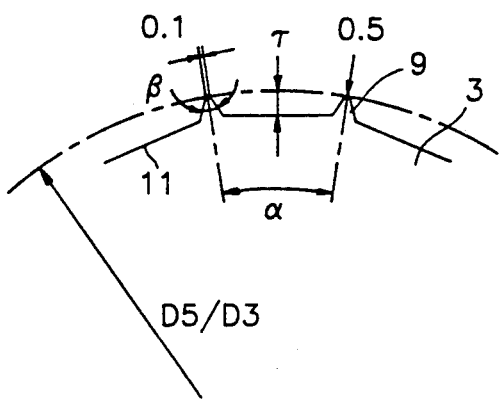

FIG. 1 schematically shows an implant 1 inserted into the bone 2. The implant has a cylindrical shaft section I on which an intermediate piece 6 is formed, at the end of which a joint piece 7, for example a ball joint, can be disposed or placed. The implant is inserted through an opening 5, formed in the bone 2, into a recess made by a tool 16, shown in FIG. 7. A shaft section II, tapering in the shape of a cone, adjoins the cylindrical shaft section I and adjoins with its surface area the inner wall of the recess formed in the bone 2. The cone-shaped shaft section II supports peripheral rows of protrusions 9 which abrade the bone 2 when the shaft 3 is inserted into it. For this purpose the surfaces or edges of the FIG. 2 is a partial section vertically to the main shaft axis A through two protrusions 9. It can be seen that the surface 11 between he protrusions has been made flat, for example with the aid of an angular milling cutter 17 shown in FIG. 5. The nose angle of the angular milling cutter 17 determines the angle of the lateral surfaces of the protrusions 9 which they enclose with the surface 11, and thus also the angle β between the lateral surfaces of the protrusions 9, having a generally triangular cross section. It can be seen from FIG. 2 that it is possible to form a curve of 0.5 mm at the point of the protrusions 9. Furthermore, the gear cutting angle α is indicated in FIG. 2 which determines the number of teeth Z, if a regular disposition of the protrusions 9 is made over the periphery of the shaft 3. A section through a protrusion 9 with concave lateral surfaces is shown in FIG. 2a.

FIG. 3 is a top view of an area of the shaft 3 with teeth 9. Visible are the generally flat surfaces 11 extending between the teeth 9, as well as semicircular surfaces 12 adjoining the surfaces 11 in the direction of the proximal end of the shaft 3, which are formed by using the angular milling cutter 17. These surfaces are of importance because they can allow the flow of body fluids and also permit the growing in of the bone and counteract the turning or pressing in of the shaft 3. The tooth surfaces 10 are located at the distal end of the protrusions 9. Advantageously the protrusions transition into a cylindrically machined area 15 of the cone-shaped shaft section II, in order to form an opportunity for a deposit of shaved off bone material because of the reduction in the cross section of the cone-shaped shaft section II in the area 15.

This development is described in FIG. 4 in a sectional view. Visible is the extension area 12, the surface 11 between the teeth 9, the abrading or cutting surface or edge 10 and the adjoining cylindrical peripheral surface 15. Instead of or additionally to this peripheral surface 15 an annular groove 14 can be formed adjoining the cutting surfaces 10.

FIG. 6 shows the disposition of various teeth 9. It should be understood that the shape of the cutting teeth can also be varied. A tooth 9 with a cutting surface 10 is visible in the upper area of FIG. 6, which includes an angle with the surface area 8 of the cone-shaped shaft section II which is considerably less than 90°. An annular groove 14 adjoins the cutting surface 10. This tooth has a back edge which is essentially parallel to the main shaft axis A and it is stepped at its proximal end.

In the center of FIG. 6 a cutting tooth 9 is shown, the cutting surface 10 of which is adjoined by a machined section 15 of the cone-shaped shaft section II. The back of the cutting tooth 9 extends inclined to the main shaft axis A. The cutting surface 10 is vertical to the surface area 8.

At the bottom of FIG. 6 a tooth 9 with a concave cutting surface 10 and concave back edge is shown.

The teeth can be produced in various ways. The most advantageous and accurate way of production is making them with the aid of a cutter head, such as shown in FIG. 5. However, other ways of producing them which if applicable, demand a smaller central angle, for example axial knurling, chiseling, percussion drilling or the like, are possible, as long as care is being taken that with these methods the distal surfaces 10 of the teeth 9 are made properly sharp in the desired way for cutting or abrading of bone material. For this reason it is advantageous if the height of the protrusions remains the same or increases towards the distal end of the shaft. A reduction in this direction would cause undesirable mechanical stresses in the bone because of displacement of the bone material laterally to the direction of the insertion of the implant. Cutting surfaces 10 which include an angle of less than 90° with the surface area 8 are advantageous, because by means of this a definite deposit of the shaved-off bone material becomes possible.

Prior to producing the teeth 9, surfaces 11, 12, annular grooves 14 and cylindrical areas 15, it is advantageous to abrade, for example by sandblasting or shot blasting, the shaft 3 so as to increase the direct support of the implant 1. Production of the teeth only takes place after sandblasting, so that they are bright and their cutting ability is not lost by abrading. If the teeth have been produced prior to sandblasting, they are to be covered during sandblasting.

It is advantageously provided that the shaft 3 has a straight, or rotation-symmetrical, distal shaft section II, tapering in the form of a cone, and an adjoining cylindrical proximal shaft section I supporting the intermediate piece 6, the aspect ratio (i.e., length to length ratio) of the cylindrical shaft section I to the cone-shaped section II being in the range of 0.2 to 0.4, preferably 0.25 to 0.35, or the ratio of the differences of the diameters (D-d), measured at the respective ends of the cone-shaped shaft section II, to the length of the cone-shaped shaft section II being in the range of 1:8 to 1:12, preferably 1:9 to 1:11. It is practical in this connection if the length of the protrusions 9 measured in the direction of the main shaft axis A is approximately 1/40 to 1/20 of the length of the cone-shaped shaft section II. It is also practical if the edge angle between the lateral surfaces 13 of the protrusions 9 is 60° to 80°, in particular 70°.

It should be understood that an irregular distribution of the teeth over the shaft 3 or the cone-shaped shaft section II is also possible. However, not too many teeth should be provided because of the stress on the bone caused thereby. Short, and not high teeth are preferred, because in this case the position of the implant is determined by the surface area adjoining the inner wall of the recess and not by the teeth adjoining the bone.

As material for the implant, alloys on a Co base and Ti alloys with Al, V, Fe, Mo or the like are mainly suitable.

What is claimed is:

1. A bone implant for insertion in a prepared recess of a human joint, said implant including an elongate shaft having proximal and distal ends configured for insertion in the recess, said shaft having a portion with a cross-sectional area that increases over the length of said portion generally in the form of a truncated cone, a joint element at the proximal end of the shaft, and a plurality of circumferentially spaced, short, lengthwise extending protrusions arranged in a circumferential ring on the shaft, the protrusions having distal end teeth for cutting-/abrading the bone when the shaft is inserted in said recess.

2. An implant as defined in claim 1 wherein each protrusion has a length which is shorter than the length of said portion of the shaft by a factor in the order of tens.

3. An implant as defined in claim 2 wherein said factor is in a range 20–40.

4. An implant as defined in claim 1 wherein the shaft has a cylindrical section between said portion and the proximal end, said portion being longer than he cylindrical section.

5. An implant as defined in claim 1 wherein the protrusions are disposed in first and second axially spaced circumferential rings.

6. An implant as defined in claim 1 wherein the teeth each have a concave cutting surface.

7. An implant as defined in claim 1 wherein the protrusions each have a height which increases along the length of the protrusion towards the distal end of the shaft.

8. An implant as defined in claim 4 having an aspect ratio of the cylindrical section to said portion in a range 0.2 to 0.4.

9. An implant as defined in claim 8 wherein the aspect ratio is in a range 0.25 to 0.35.

10. An implant as defined in claim 4 including two circumferential rings of said protrusions on said portion of the shaft, said rings being at locations about one third and two thirds of the length of said portion respectively from one end of said portion.

11. An implant as defined in claim 1 wherein said portion o the shaft has a larger diameter at one end thereof, and a smaller diameter at an opposite end thereof and wherein a ratio between the difference of said diameters and the length of said portion is in a range 8:1 to 12:1.

12. An implant as defined in claim 11 wherein said ratio is in a range 9:1 to 11:1.

13. An implant as defined in claim 1 wherein the protrusions have a height in a range 0.2 to 1 mm.

14. An implant as defined in claim 13 wherein the height is in a range 0.3 to 0.6 mm.

15. An implant as defined in claim 1 wherein the protrusions are circumferentially spaced apart at angles in a range 10° to 35°.

16. An implant as defined in claim 15 wherein the range is 15° to 30°.

17. An implant as defined in claim 5 wherein the protrusions are arranged with equal angles therebetween.

18. An implant as defined in claim 1 wherein the protrusions are substantially triangular in cross-section with an apex angle in a range 60° to 80°.

19. An implant as defined in claim 18 wherein the apex angle is about 70°.

20. An implant as defined in claim 1 wherein the shaft has a annular groove adjacent said ring at the distal ends of the protrusions.

21. An implant as defined in claim 1 wherein the shaft has a cylindrical portion extending from the distal end of the ring to a length approximating the length of the protrusions.

22. An implant as defined in claim 21 including an annular groove in said cylindrical portion adjacent the distal end of the ring.

23. An implant as defined in claim 1 wherein the shaft has flat surfaces between the protrusions.

24. An implant as defined in claim 21 wherein said surfaces have arcuate shape extensions at a proximal end of the ring.

25. An implant as defined in claim 1 wherein the protrusions are arranged in axially spaced circumferential rings on said portion of the shaft, the spacing between the rings being four to six times the length of the protrusions.

26. An implant as defined in claim 4 wherein the protrusions are located both on said portion of the shaft and on said cylindrical section of the shaft.

27. An implant as defined in claim 1 wherein the protrusions extend at least in part, substantially parallel to the shaft axis.

28. An implant as defined in claim 1 wherein the shaft includes a longitudinal bore.

* * * * *